US011707600B2

(12) United States Patent
Snipelisky et al.

(10) Patent No.: US 11,707,600 B2
(45) Date of Patent: Jul. 25, 2023

(54) LEVEL SET CALIBRATION AND ASSURANCE FOR PULMONARY ARTERY PRESSURE CATHETERIZATION

(71) Applicant: CardioDriven, Inc., Parkland, FL (US)

(72) Inventors: David F. Snipelisky, Parkland, FL (US); Jonathan Hack, Parkland, FL (US); Joshua Friedman, Parkland, FL (US)

(73) Assignee: CARDIODRIVEN, INC., Parkland, FL (US)

( * ) Notice: Subject to any disclaimer, the term of this patent is extended or adjusted under 35 U.S.C. 154(b) by 464 days.

(21) Appl. No.: 16/952,028

(22) Filed: Nov. 18, 2020

(65) Prior Publication Data

US 2022/0152350 A1    May 19, 2022

(51) Int. Cl.
| | |
|---|---|
| *G08B 21/02* | (2006.01) |
| *A61M 25/01* | (2006.01) |
| *A61B 5/0215* | (2006.01) |
| *A61B 5/06* | (2006.01) |
| *A61B 5/00* | (2006.01) |
| *A61M 25/00* | (2006.01) |

(52) U.S. Cl.
CPC ..... *A61M 25/0105* (2013.01); *A61B 5/02156* (2013.01); *A61B 5/061* (2013.01); *A61B 5/746* (2013.01); *A61B 2560/0223* (2013.01); *A61M 2025/0001* (2013.01); *A61M 2025/0166* (2013.01); *A61M 2205/18* (2013.01); *A61M 2205/3592* (2013.01); *A61M 2205/502* (2013.01); *A61M 2205/52* (2013.01); *A61M 2205/70* (2013.01)

(58) Field of Classification Search
USPC ....... 340/573.1, 539.12, 286.07, 7.59, 691.3, 340/691.6, 539.22, 472
See application file for complete search history.

(56) References Cited

U.S. PATENT DOCUMENTS

| | | | |
|---|---|---|---|
| 2007/0021678 A1* | 1/2007 | Beck | A61B 5/0245 600/513 |
| 2013/0289641 A1* | 10/2013 | Gustafsson | A61N 1/36571 607/18 |
| 2013/0316977 A1* | 11/2013 | Steen | A61K 33/14 514/59 |
| 2017/0239407 A1* | 8/2017 | Hayward | A61M 60/523 |
| 2019/0175858 A1* | 6/2019 | Parfenova | A61M 16/10 |

* cited by examiner

*Primary Examiner* — Daniel Previl
(74) *Attorney, Agent, or Firm* — CRGO Global; Steven M. Greenberg

(57) ABSTRACT

Embodiments of the present invention provide for maintaining a level set of a pulmonary artery catheterization apparatus that includes a pulmonary artery pressure sensor in communication with a pulmonary artery catheterization manifold affixed to a pulmonary artery catheter. The method includes calibrating leveling of the pulmonary artery pressure sensor (at the level of the right atrium) with the pulmonary artery catheterization manifold by recording a vertical level of a leveling base positioned at a common level to the manifold, relative to a vertical level of a leveling sensor positioned at a common level to the pulmonary artery pressure sensor. The method further includes monitoring a difference between the recorded vertical level of the leveling base relative to the vertical level of the leveling sensor. Finally, the method includes generating an alert in a user interface element of the leveling sensor in response to the monitored difference exceeding a threshold value.

18 Claims, 2 Drawing Sheets

LEVEL SET CALIBRATION AND ASSURANCE FOR PULMONARY ARTERY PRESSURE CATHETERIZATION

BACKGROUND OF THE INVENTION

Field of the Invention

The present invention relates to the field of pulmonary artery catheterization and more particularly to ensuring a level condition between patient and pressure sensor during pulmonary artery catheterization.

Description of the Related Art

Pulmonary artery catheterization, also known as right heart catheterization, refers to the insertion of a catheter into the right-sided heart chambers and pulmonary artery. The purpose of pulmonary artery catheterization is diagnostic in that pulmonary artery catheterization can be used to detect heart failure or sepsis, monitor therapy, and evaluate the effects of administered drugs. In furtherance of such diagnostics, a pulmonary artery catheter allows for the direct, simultaneous measurement of hemodynamics—namely the pressure in the right atrium, the pressure in the right ventricle, the pressure of the pulmonary artery, and the filling pressure of the left atrium.

The apparatus generally used to accommodate the measurement of pulmonary hemodynamics through pulmonary artery catheterization includes several components. Specifically, the apparatus includes the actual pulmonary artery catheter inserted into the patient, generally through a central vein, as well as an external manifold coupled both to the catheter and to a pressure transducer. The pressure transducer then allows for the alternate transduction of the intracardiac pressures from the pulmonary artery catheter into a measurable electrical signal. The external manifold permits an alteration between a pressure sensing mode and calibration mode in which the pressure reading of the transducer using atmospheric pressure is recorded so as to "zero out" the pressure readings of the transducer. The manifold remains external to the patient and is generally mounted to an intravenous pole adjacent to the patient.

In so far as the pressure sensor reads pressures with in the right atrium of the heart, the external pressure sensor ideally is to remain on a level horizontal plane with the right atrium of the patient. If the pressure sensor falls out of alignment with the horizontal plane of the right atrium, the pressure readings that are subsequently obtained are likely to be inaccurate. Presently, the primary method to "zero out" the pressure transducer of the manifold, with the pulmonary artery catheter at the level of the right atrium includes the manual manipulation with use of a ruler or other measuring stick or through the use of other manual measurement devices, including the use of a laser pointer.

BRIEF SUMMARY OF THE INVENTION

Embodiments of the present invention address deficiencies of the art in respect to pulmonary artery catheterization calibration and provide a novel and non-obvious method, system and computer program product for maintaining a level set of a pulmonary artery catheterization apparatus that includes an external pulmonary artery pressure sensor in communication with a pulmonary artery catherization manifold affixed to a pulmonary artery catheter. In an embodiment of the invention, a method for maintaining a level set of a pulmonary artery catheterization apparatus includes calibrating a leveling of the external pulmonary artery pressure sensor with the pulmonary artery catheterization manifold by recording a vertical level of a leveling base positioned at a common level to the manifold, relative to a vertical level of a leveling sensor positioned at a common level to the pulmonary artery pressure sensor. The method further includes monitoring a difference between the recorded vertical level of the leveling base relative to the vertical level of the leveling sensor. Finally, the method includes generating an alert in a user interface element of the leveling sensor in response to the monitored difference exceeding a threshold value.

In one aspect of the embodiment, the calibration includes sensing both a vertical level of the leveling base and also a vertical level of the leveling sensor and comparing the sensed vertical level of the leveling base to the sensed vertical level at the leveling sensor. The comparison is then repeated until the sensed vertical level of the leveling base is determined to be within a threshold of the sensed vertical level of the leveling sensor. Thereafter, in response to a determination that the sensed vertical level of the leveling base is within the threshold of the sensed vertical level of the leveling sensor, a notification may be emitted in a user interface element of the leveling sensor. This allows for accurate readings of the intracardiac pressures by way of ensuring appropriate leveling on the same horizontal place of the intracardiac pulmonary artery catheter apparatus with the external manifold.

Of note, the leveling base can be a junction box, or other similarly functioning measurement tool, fluidly communicatively coupled to the leveling sensor by way of a closed fluid channel to which the junction box as secured at a distal end and to which the leveling sensor is secured at a proximal end, and including a hydrophobic filter at an opposite side of the junction box relative to a side at which the closed fluid channel is secured. In this scenario, then, the calibration includes establishing a bolus of gas within the closed fluid channel proximate to the junction box, sensing a pressure reading at the leveling sensor and recording the sensed pressure reading as the monitored difference between the recorded vertical level of the leveling base relative to the vertical level of the leveling sensor.

Alternatively, the leveling base can be an optical range finder. In this scenario, the calibration includes emitting an optical signal from a top surface of the range finder, receiving a reflection of the optical signal in the range finder, computing a distance of the leveling base from a surface from which the optical signal has reflected and computing the vertical level of the leveling base as a function of the computed distance. Similarly, the leveling base can be a sonic range finder, such that the calibration includes emitting an ultrasonic signal from a top surface of the range finder, receiving a reflection of the ultrasonic signal in the range finder, computing a distance of the leveling base from a surface from which the ultrasonic signal has reflected and computing the vertical level of the leveling base as a function of the computed distance.

Finally, in yet another aspect of the embodiment, the leveling base can include an ultrasonic signal emitter and the leveling sensor can include an ultrasonic signal receiver. In this scenario, the calibration can include emitting an ultrasonic signal from signal emitter, receiving the ultrasonic signal in the signal receiver and repeatedly computing a strength of the signal at the signal receiver as either or both of the leveling base and the leveling sensor are adjusted vertically. Thereafter, the vertical level of the leveling base may be computed as the vertical level of the leveling sensor when a strength of the received ultrasonic signal peaks so that a weakening of the strength of the received ultrasonic signal at the signal receiver indicates a vertical movement of the pulmonary artery catheterization manifold out of vertical alignment with the vertical level of the pressure receiver.

In another embodiment of the invention, a pulmonary artery catheterization apparatus leveling data processing system can be adapted for use with a pulmonary artery pressure sensor in communication with a pulmonary artery catherization manifold affixed to a pulmonary artery catheter. The system can include a host computing platform of one or more computers, each with memory and at least one processor. The system also can include a leveling sensor electrically communicatively coupled to the host computing platform and positioned at a common level to the pulmonary artery pressure sensor. The system yet further can include a leveling base communicatively coupled to the leveling sensor and positioned at a common level to the manifold.

Finally, the system can include a level set maintenance module stored in the host computing platform. The module includes computer program instructions enabled while executing in the host computing platform to calibrate a leveling of the pulmonary artery pressure sensor with the pulmonary artery catheterization manifold by recording a vertical level of a leveling base relative to a vertical level of the leveling sensor and monitoring a difference between the recorded vertical level of the leveling base relative to the vertical level of the leveling sensor. The program instructions then generate an alert in a user interface element of the leveling sensor in response to the monitored difference exceeding a threshold value.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for maintaining a level set of a pulmonary artery catheter. In accordance with an embodiment of the invention, the level set of a pulmonary artery catheterization apparatus can be maintained by recording a relative vertical level of a leveling base affixed to a chest surface or at a point on the body of an external landmark of the right atrium of a patient adjacent to a pulmonary artery catherization manifold, and in respect to a vertical level of a leveling sensor adjacent to a pressure sensor for the manifold. Then, a difference may be monitored between the recorded vertical levels. To the extent that the monitored difference exceeds a threshold value, an alert may be generated in a user interface element of the apparatus so as to indicate the falling out of level set of the apparatus and the requirement to re-level set the apparatus in order to achieve accurate hemodynamic pressure measurements through the apparatus.

Figure 1:
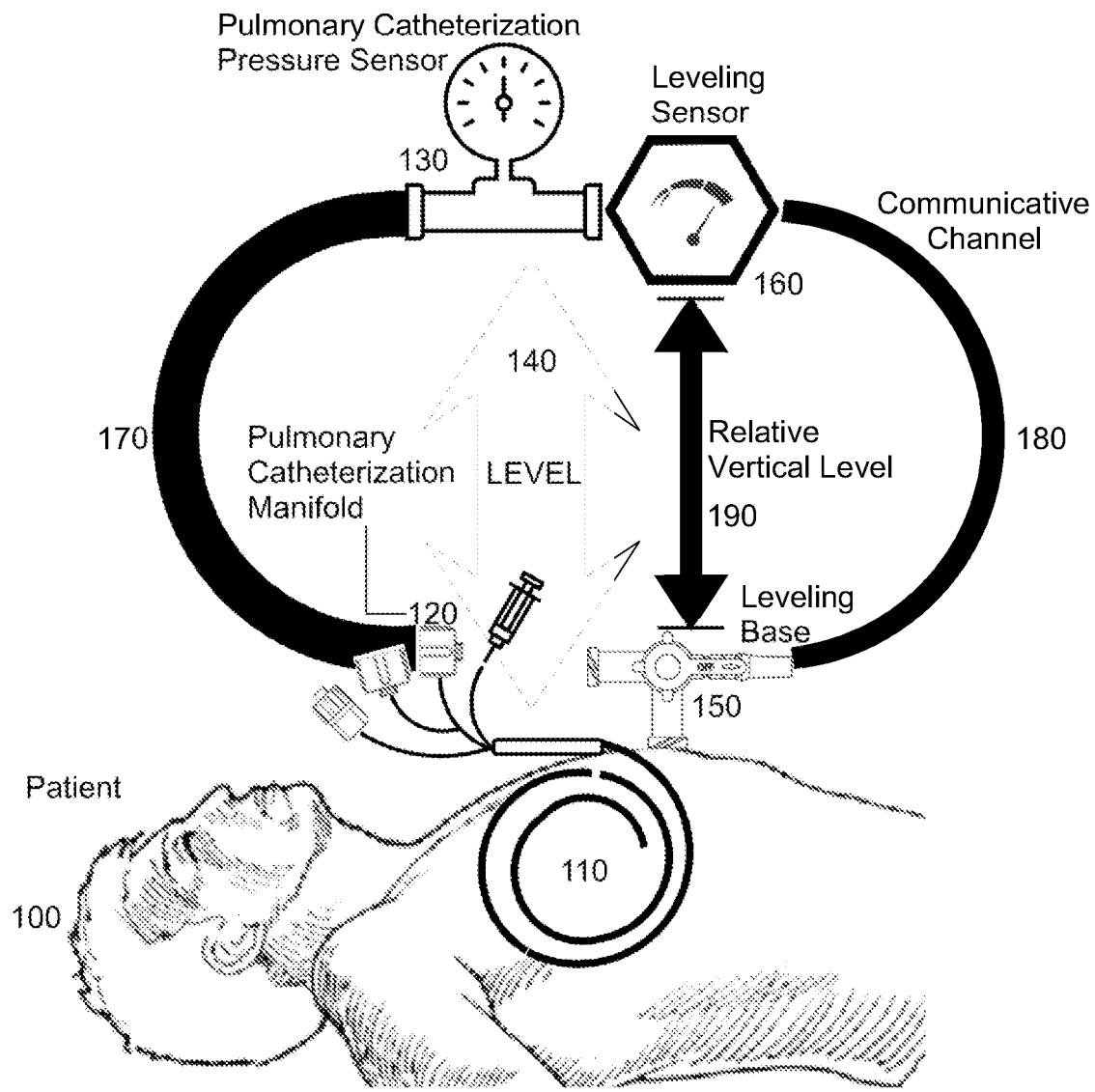
FIG. 1 is pictorial illustration of a process for maintaining a level set of a pulmonary artery catheterization apparatus.

In further illustration, FIG. 1 is pictorial illustration of a process for maintaining a level set of a pulmonary artery catheterization apparatus. As shown in FIG. 1, a leveling base 150 is placed adjacent on an external landmark of the right atrium of the body to the manifold 120 of a pulmonary catheter 110 inserted into the central venous system, and subsequently right sided heart chambers and pulmonary artery, of a patient 100. A communicative channel 180 is then established between the leveling base 150 and a leveling sensor 160 positioned adjacent to and at the same level as a pulmonary artery catherization pressure sensor 130 fluidly communicatively linked to the manifold 120 by way of hollow tube 170. The communicative channel 180 can include a fluid filled tube with a bolus disposed at a distal end of the tube adjacent to the leveling base 150, which in this instance can be a junction box, stopcock or similar system, with a hydrophobic filter separating the tube from an interior portion of the tubing. Alternatively, the communicative channel 180 can a wireless communications channel over which wireless signals may be exchanged between the leveling base 150 and the leveling sensor 160. As yet another alternative, the communicative channel 180 can be a wire bound electrical channel over which electrical signals may be exchanged between the leveling base 150 and the leveling sensor 160.

In operation, the level set 140 of the manifold 120 and the pulmonary catheterization pressure sensor 130 may be established so that the manifold 120 and the pulmonary catheterization pressure sensor 130 are at an equal distance from a floor (on the same horizontal plane, at the same vertical height) over which the patient 100 is positioned. The level set 140 may be initially determined manually with the assistance of a measuring stick, or with the observation of a bolus within the communicative channel 180 so as to assure the position of the bolus at the distal end of the communicative channel 180 at the leveling base 150, or the level sensor 160 can be placed next to the leveling base 150 at the same vertical height and the leveling sensor 160 be calibrated at the same vertical height, thus the level set 140, as the leveling base 150 followed by the leveling base 150 subsequently attached to the patient at the level of the right atrium and the leveling sensor 160, with the pulmonary catheterization pressure sensor 130, re-positioned on an external intravenous pole and adjusted accordingly to adjust to a level set 140. Thereafter, a change in the level set 140 may be detected, for instance by a reading received from an accelerometer (not shown) affixed to either or both of the pulmonary catheterization pressure sensor 130 and the manifold 120.

Responsive to a detection of a change in the level set 140, a pressure reading at the leveling sensor 160 may be recorded as the pressure associated with the level set 140. Alternatively, the level set 140 may be determined by independently computing a vertical level of each of the leveling base 150 and the leveling sensor 160 and a comparison of the two to produce a relative vertical level 190 which, if within a threshold value, can be presumed to reflect the level set 140.

In regard to the latter, the vertical level of the leveling sensor 160 can be pre-determined based upon measurement features of a fixture such as an IV pole to which the leveling sensor 160 and the pulmonary catheterization pressure sensor 130 are secured. Then, the vertical level of the leveling base 150 can be determined through range finding, such as ultrasonic range finding of the distance of the leveling base 150 to the ceiling, or the optical range finding of the distance of the leveling base 150 to the ceiling, so the knowledge of the height of the ceiling relative to the floor can produce the vertical level of the leveling base 150.

Once the level set 140 is established, a deviation in the relative vertical level 190 may be detected. For instance, in the case where a pressure reading in the leveling sensor 160 has been associated with the relative vertical level 190 for the level set 140, a change in the pressure reading beyond a threshold value can be trigger the display of an alert in a user interface to the leveling sensor 160. Alternatively, in the case where the relative vertical level 190 is produced as a comparison between two determined vertical levels of the leveling base 150 and the leveling sensor 160, respectively, a threshold change in the relative vertical level 190 can trigger a display of an alert in a user interface to the leveling sensor 160. In this way, the level set 140 can be maintained so as to produce accurate pressure readings at the pulmonary catheterization pressure sensor 130 and, when the pulmonary catheterization pressure sensor 130 falls out of the level set 140 with respect to the manifold 120, an operator can be alerted to such fact so that corrective measures (e.g. returning to level set 140) may be undertaken.

Figure 2:
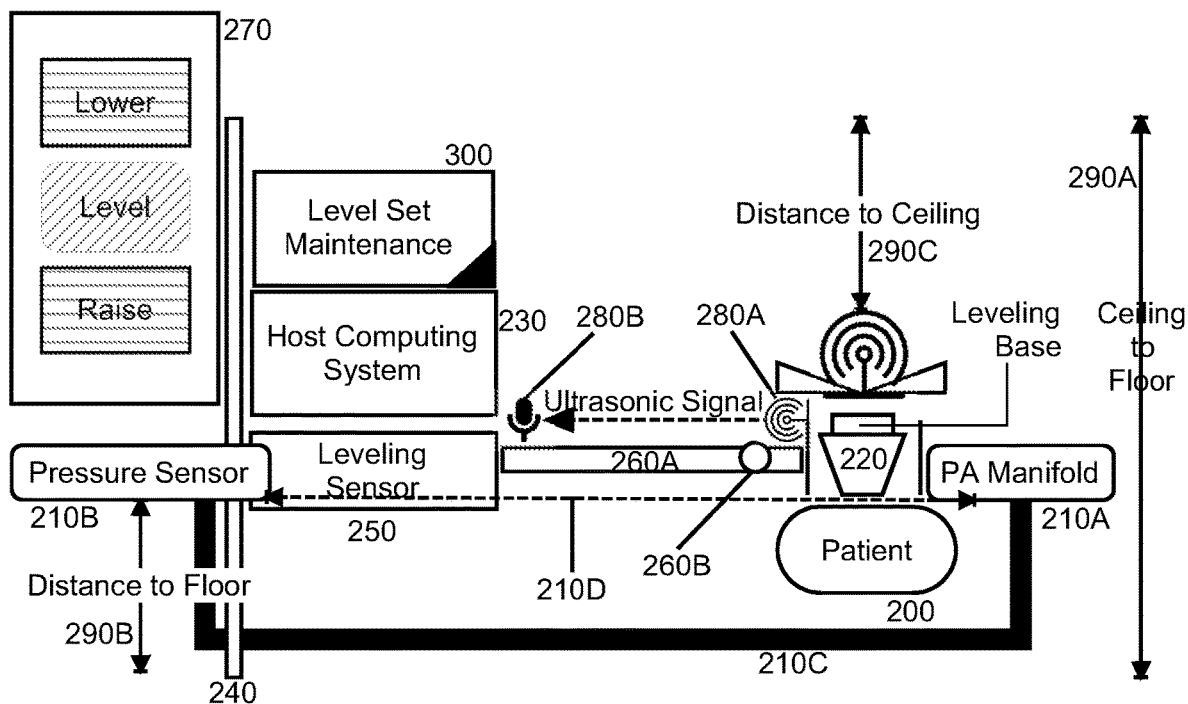
FIG. 2 is a schematic illustration of a data processing system adapted for maintaining level set in a pulmonary catheterization apparatus; and, FIG. 3 is a flow chart illustrating a process for maintaining a level set of a pulmonary artery catheterization apparatus.

The process described in connection with FIG. 1 may be implemented within a data processing system. In further illustration, FIG. 2 schematically shows a data processing system adapted for maintaining level set in a pulmonary catheterization apparatus. The system includes a leveling base 220 positioned adjacent to a pulmonary artery catheterization manifold 210A proximate to a chest surface of a patent 200, and communicatively coupled to a leveling sensor 250 fixed at a same level on an IV pole 240 as a pulmonary artery catheterization pressure sensor 210B sensing pressure readings from the manifold 210A by way of a fluid channel 210C fixed therebetween.

The leveling base 220 and the leveling sensor 250 communicate with one another over communications channel 260A. In one aspect of the embodiment, the communications channel 260A can be a fluid communications channel, e.g. a tube, in which a liquid such as saline has been injected so as to produce a bolus 260B at a distal end of the tube when the leveling base 220 is at a common vertical level with the leveling sensor 250 secured to a proximal end of the tube. In this aspect of the embodiment, the leveling base 220 is a junction box with a hydrophobic filter at an opposite side of the junction box relative to the distal end of the tube or alternatively, the leveling base 220 is a stopcock or similar apparatus, with a port alternately open to atmosphere when another port is closed to a luer lock, and closed to atmosphere when the other port is open to the luer lock.

In an alternative aspect of the embodiment, the leveling base 220 includes a range finder 215 adapted to compute a distance 290C of the range finder 215 from a reflecting surface such as a ceiling or floor. The range finder 215 can make such determination by emitting light wave or ultrasonic signals which reflect back to the range finder 215. In yet another alternative aspect of the embodiment, a signal emitter 280A may be affixed to the leveling base 220 and a signal receiver 280B may be affixed to the leveling sensor 250 so that the signal receiver 280B may receive emitted signals from the signal emitter 280A and assess a strength of the received signals.

Notably, a host computing system 230 is coupled to the leveling sensor 250 and secured to the IV pole 240. The host computing system 230 includes one or more computers, each with memory and at least one processor, and supports the operation of a level set maintenance module 300. The level set maintenance module 300 includes computer program instructions that when executing in the memory of the host computing platform 230, are enabled to record level set 210D for the pulmonary artery catheterization manifold 210A relative to the pulmonary artery catheterization pressure sensor 210B, either by recording a pressure reading at the leveling sensor 250 when the bolus 260B is proximate to the exterior portion of the leveling base 220, or by recording a relative vertical level within a threshold value of the leveling base 220 and the leveling sensor 250.

In respect to the latter, in one aspect of the embodiment, the program instructions are enabled to receive a range value from the range finder 215 and to derive a vertical level of the leveling base 220 as a difference between a known ceiling height 290A and the range 290C provided by the range finder 215 between the ceiling and the leveling base 220. Then, the program instructions can compare the derived vertical level of the leveling base 220 with the known vertical level 290B of the leveling sensor. To the extent that the derived vertical level is within a threshold value of the known vertical level 290B, level set 210D is presumed and the program instructions present a graphical indication in a user interface 270 to the leveling sensor 250. Otherwise, the program instructions repeatedly compute the derived vertical level of the leveling base 220 and direct a presentation of a corrective action in the user interface 270 as the vertical level of the patient may be adjusted until the program instructions determine that level set 210D has been established.

In another aspect of the embodiment, in which the signal emitter 280A communicates with the signal receiver 280B, the program instructions are enabled to process the receipt of an emitted ultrasonic signal from the emitter 280A at the receiver 280B and to measure the received signal strength. The program instructions the compute a difference between the measured signal strength and the known signal strength when level set 210D is established so as to either direct a corrective action in the user interface 270, or to indicate that level set 210D is established.

Thereafter, the program instructions can repeatedly measure the signal strength of the signal emitted from the emitter 280A with a threshold weakening of the strength of the signal indicating a failure to maintain the level set 210D. Likewise, as to the aspect of the embodiment in which a range finder 215 is employed, the program instructions can repeatedly measure the distance to the ceiling 290C and to derive the vertical level of the leveling base 220 so that a threshold differential between the derived vertical level and the known vertical level 290B indicates a failure to maintain the level set 210D. Finally, as to the aspect of the embodiment in which a reference pressure is detected in the leveling sensor 250 when the bolus is proximate to the exterior portion of the leveling base 220, the program instructions can repeatedly measure the pressure in the channel 260A so that a threshold change in the pressure indicates a failure to maintain the level set 210D.

Figure 3:
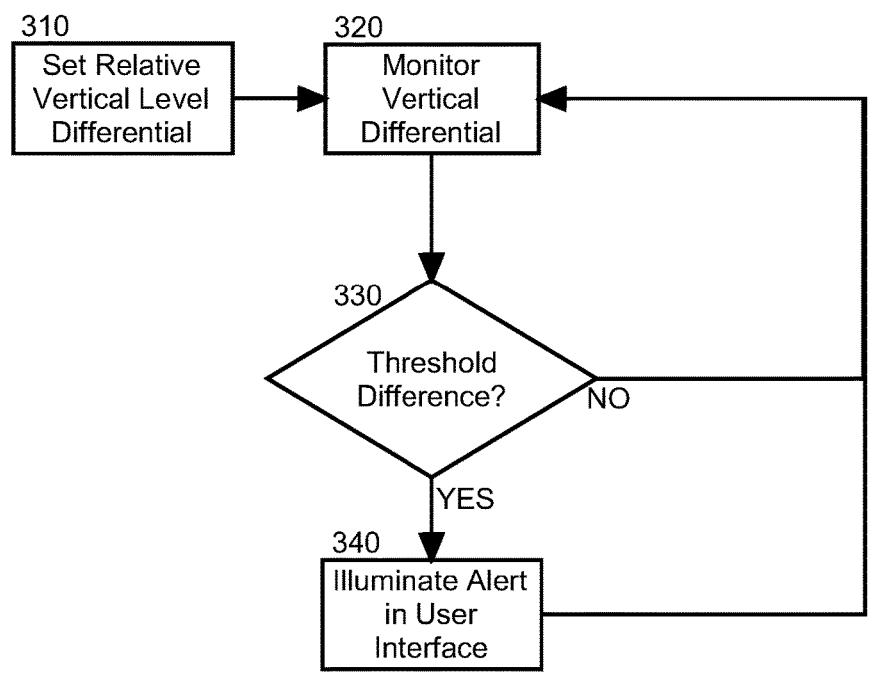

In even yet further illustration of the operation of the level set maintenance module 300, FIG. 3 is a flow chart illustrating a process for maintaining a level set of a pulmonary artery catheterization apparatus. Beginning in block 310, a relative vertical level differential between a leveling base and a leveling sensor is recorded for level set of pulmonary artery catheterization manifold with respect to a corresponding pulmonary artery catheterization pressure sensor. For instance, the differential may be recorded as a specific pressure value of pressure in a fluid communications channel between the leveling base and the leveling sensor, or a signal strength of a wireless signal transmitted between the leveling base and the leveling sensor, or a difference between a derived vertical level of the leveling base and a known vertical level of the leveling sensor. Then, in block 320, the vertical differential is monitored for threshold changes. In decision block 330, if a threshold different in the vertical differential is detected, in block 340, an alert is presented in a user interface to the leveling sensor.

The present invention may be embodied within a system, a method, a computer program product or any combination thereof. The computer program product may include a computer readable storage medium or media having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network. The computer readable program instructions may execute entirely on the user's computer, partly on the user's computer, as a stand-alone software package, partly on the user's computer and partly on a remote computer or entirely on the remote computer or server. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which includes one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Finally, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "include", "includes", and/or "including," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A method for maintaining a level set of a pulmonary artery catheterization apparatus comprising a pulmonary artery pressure sensor in communication with a pulmonary artery catherization manifold affixed to a pulmonary artery catheter at the same horizontal plane as the right atrium of the heart, the method comprising:
   calibrating a leveling of the pulmonary artery pressure sensor with the pulmonary artery catheterization manifold by recording a vertical level of a leveling base positioned at a common level to the manifold, relative to a vertical level of a leveling sensor positioned at a common level to the pulmonary artery pressure sensor;
   monitoring a difference between the recorded vertical level of the leveling base relative to the vertical level of the leveling sensor; and,
   generating an alert in a user interface element of the leveling sensor in response to the monitored difference exceeding a threshold value.

2. The method of claim 1, wherein the calibration comprises:
   sensing both a vertical level of the leveling base and also a vertical level of the leveling sensor;
   comparing the sensed vertical level of the leveling base to the sensed vertical level at the leveling sensor and repeating the comparison until the sensed vertical level of the leveling base is determined to be within a threshold of the sensed vertical level of the leveling sensor; and,
   responsive to the determination that the sensed vertical level of the leveling base is within the threshold of the sensed vertical level of the leveling sensor, emitting a notification in the user interface element of the leveling sensor.

3. The method of claim 1, wherein the leveling base is a junction box fluidly communicatively coupled to the leveling sensor by way of a closed fluid channel to which the junction box as secured at a distal end and to which the leveling sensor is secured at a proximal end, the junction box including a hydrophobic filter at an opposite side of the junction box relative to a side at which the closed fluid channel is secured, the calibration comprising:
   establishing a bolus of gas within the closed fluid channel proximate to the junction box;
   sensing a pressure reading at the leveling sensor; and,
   recording the sensed pressure reading as the monitored difference between the recorded vertical level of the leveling base relative to the vertical level of the leveling sensor.

4. The method of claim 1, wherein the leveling base comprises an optical range finder, the calibration comprising:
   emitting an optical signal from a top surface of the range finder;
   receiving a reflection of the optical signal in the range finder;
   computing a distance of the leveling base from a surface from which the optical signal has reflected; and,
   computing the vertical level of the leveling base as a function of the computed distance.

5. The method of claim 1, wherein the leveling base comprises a sonic range finder, the calibration comprising:
   emitting an ultrasonic signal from a top surface of the range finder;
   receiving a reflection of the ultrasonic signal in the range finder;
   computing a distance of the leveling base from a surface from which the ultrasonic signal has reflected; and,
   computing the vertical level of the leveling base as a function of the computed distance.

6. The method of claim 1, wherein the leveling base comprises an ultrasonic signal emitter and wherein the leveling sensor comprises an ultrasonic signal receiver, the calibration comprising:
   emitting an ultrasonic signal from signal emitter;
   receiving the ultrasonic signal in the signal receiver;
   repeatedly computing a strength of the signal at the signal receiver as either or both of the leveling base and the leveling sensor are adjusted vertically; and,
   computing the vertical level of the leveling base as the vertical level of the leveling sensor when a strength of the received ultrasonic signal peaks so that a weakening of the strength of the received ultrasonic signal at the signal receiver indicates a vertical movement of the pulmonary artery catheterization manifold out of vertical alignment with the vertical level of the pressure receiver.

7. A pulmonary artery catheterization apparatus leveling data processing system adapted for use with a pulmonary artery pressure sensor in communication with a pulmonary artery catherization manifold affixed to a pulmonary artery catheter, the system comprising:
   a host computing platform comprising one or more computers, each comprising memory and at least one processor;
   a leveling sensor electrically communicatively coupled to the host computing platform and positioned at a common level to the pulmonary artery pressure sensor;
   a leveling base communicatively coupled to the leveling sensor and positioned at a common level to the manifold; and,
   a level set maintenance module stored in the host computing platform and comprising computer program instructions enabled while executing in the host computing platform to perform:
      calibrating a leveling of the pulmonary artery pressure sensor with the pulmonary artery catheterization manifold by recording a vertical level of a leveling base relative to a vertical level of the leveling sensor;
      monitoring a difference between the recorded vertical level of the leveling base relative to the vertical level of the leveling sensor; and,
      generating an alert in a user interface element of the leveling sensor in response to the monitored difference exceeding a threshold value.

8. The system of claim 7, wherein the calibration comprises:
   sensing both a vertical level of the leveling base and also a vertical level of the leveling sensor;
   comparing the sensed vertical level of the leveling base to the sensed vertical level at the leveling sensor and repeating the comparison until the sensed vertical level of the leveling base is determined to be within a threshold of the sensed vertical level of the leveling sensor; and,
   responsive to the determination that the sensed vertical level of the leveling base is within the threshold of the sensed vertical level of the leveling sensor, emitting a notification in the user interface element of the leveling sensor.

9. The system of claim 7, wherein the leveling base is a junction box fluidly communicatively coupled to the leveling sensor by way of a closed fluid channel to which the junction box as secured at a distal end and to which the leveling sensor is secured at a proximal end, the junction box including a hydrophobic filter at an opposite side of the junction box relative to a side at which the closed fluid channel is secured, the calibration comprising:

establishing a bolus of gas within the closed fluid channel proximate to the junction box;

sensing a pressure reading at the leveling sensor; and, recording the sensed pressure reading as the monitored difference between the recorded vertical level of the leveling base relative to the vertical level of the leveling sensor.

10. The system of claim 7, wherein the leveling base comprises an optical range finder, the calibration comprising:

emitting an optical signal from a top surface of the range finder;

receiving a reflection of the optical signal in the range finder;

computing a distance of the leveling base from a surface from which the optical signal has reflected; and, computing the vertical level of the leveling base as a function of the computed distance.

11. The system of claim 7, wherein the leveling base comprises a sonic range finder, the calibration comprising:

emitting an ultrasonic signal from a top surface of the range finder;

receiving a reflection of the ultrasonic signal in the range finder;

computing a distance of the leveling base from a surface from which the ultrasonic signal has reflected; and, computing the vertical level of the leveling base as a function of the computed distance.

12. The system of claim 7, wherein the leveling base comprises an ultrasonic signal emitter and wherein the leveling sensor comprises an ultrasonic signal receiver, the calibration comprising:

emitting an ultrasonic signal from signal emitter;

receiving the ultrasonic signal in the signal receiver;

repeatedly computing a strength of the signal at the signal receiver as either or both of the leveling base and the leveling sensor are adjusted vertically; and, computing the vertical level of the leveling base as the vertical level of the leveling sensor when a strength of the received ultrasonic signal peaks so that a weakening of the strength of the received ultrasonic signal at the signal receiver indicates a vertical movement of the pulmonary artery catheterization manifold out of vertical alignment with the vertical level of the pressure receiver.

13. A computer program product for maintaining a level set of a pulmonary artery catheterization apparatus comprising a pulmonary artery pressure sensor in communication with a pulmonary artery catherization manifold affixed to a pulmonary artery catheter, the computer program product including a computer readable storage medium having program instructions embodied therewith, the program instructions executable by a device to cause the device to perform a method including:

calibrating a leveling of the pulmonary artery pressure sensor with the pulmonary artery catheterization manifold by recording a vertical level of a leveling base positioned at a common level to the manifold, relative to a vertical level of a leveling sensor positioned at a common level to the pulmonary artery pressure sensor;

monitoring a difference between the recorded vertical level of the leveling base relative to the vertical level of the leveling sensor; and, generating an alert in a user interface element of the leveling sensor in response to the monitored difference exceeding a threshold value.

14. The computer program product of claim 13, wherein the calibration comprises:

sensing both a vertical level of the leveling base and also a vertical level of the leveling sensor;

comparing the sensed vertical level of the leveling base to the sensed vertical level at the leveling sensor and repeating the comparison until the sensed vertical level of the leveling base is determined to be within a threshold of the sensed vertical level of the leveling sensor; and, responsive to the determination that the sensed vertical level of the leveling base is within the threshold of the sensed vertical level of the leveling sensor, emitting a notification in the user interface element of the leveling sensor.

15. The computer program product of claim 13, wherein the leveling base is a junction box fluidly communicatively coupled to the leveling sensor by way of a closed fluid channel to which the junction box as secured at a distal end and to which the leveling sensor is secured at a proximal end, the junction box including a hydrophobic filter at an opposite side of the junction box relative to a side at which the closed fluid channel is secured, the calibration comprising:

establishing a bolus of gas within the closed fluid channel proximate to the junction box;

sensing a pressure reading at the leveling sensor; and, recording the sensed pressure reading as the monitored difference between the recorded vertical level of the leveling base relative to the vertical level of the leveling sensor.

16. The computer program product of claim 13, wherein the leveling base comprises an optical range finder, the calibration comprising:

emitting an optical signal from a top surface of the range finder;

receiving a reflection of the optical signal in the range finder;

computing a distance of the leveling base from a surface from which the optical signal has reflected; and, computing the vertical level of the leveling base as a function of the computed distance.

17. The computer program product of claim 13, wherein the leveling base comprises a sonic range finder, the calibration comprising:

emitting an ultrasonic signal from a top surface of the range finder;

receiving a reflection of the ultrasonic signal in the range finder;

computing a distance of the leveling base from a surface from which the ultrasonic signal has reflected; and, computing the vertical level of the leveling base as a function of the computed distance.

18. The computer program product of claim 13, wherein the leveling base comprises an ultrasonic signal emitter and wherein the leveling sensor comprises an ultrasonic signal receiver, the calibration comprising:
- emitting an ultrasonic signal from signal emitter;
- receiving the ultrasonic signal in the signal receiver;
- repeatedly computing a strength of the signal at the signal receiver as either or both of the leveling base and the leveling sensor are adjusted vertically; and,
- computing the vertical level of the leveling base as the vertical level of the leveling sensor when a strength of the received ultrasonic signal peaks so that a weakening of the strength of the received ultrasonic signal at the signal receiver indicates a vertical movement of the pulmonary artery catheterization manifold out of vertical alignment with the vertical level of the pressure receiver.

* * * * *